United States Patent [19]

Ohsaki et al.

[11] Patent Number: 5,075,474
[45] Date of Patent: Dec. 24, 1991

[54] METHOD FOR PREPARING HEXAMETHYL CYCLOTRISILAZANE

[75] Inventors: Hiromi Ohsaki; Yoshihumi Takeda; Toshinobu Ishihara, all of Joetsu; Akira Hayashida, Higashimurayama, all of Japan

[73] Assignee: Shin-Etsu Chemical Co., Ltd., Japan

[21] Appl. No.: 679,199

[22] Filed: Apr. 2, 1991

[30] Foreign Application Priority Data

Apr. 20, 1990 [JP] Japan .................................. 2-104888

[51] Int. Cl.⁵ .............................................. C07F 7/10
[52] U.S. Cl. ..................................................... 556/409
[58] Field of Search ......................................... 556/409

[56] References Cited

U.S. PATENT DOCUMENTS

| | | | |
|---|---|---|---|
| 3,481,964 | 12/1969 | Ismail et al. | 556/409 X |
| 3,655,711 | 4/1972 | Bush et al. | 556/409 |
| 3,677,977 | 7/1972 | Bush et al. | 556/409 X |
| 4,577,039 | 3/1986 | Arkles et al. | 556/409 |
| 4,855,469 | 8/1989 | Baile et al. | 556/409 |

Primary Examiner—Paul F. Shaver
Attorney, Agent, or Firm—Parkhurst, Wendel & Rossi

[57] ABSTRACT

According to the method for preparing hexamethyl cyclotrisilazane of the present invention, hexamethyl cyclotrisilazane can be obtained by heating a linear or cyclic silazane compound represented by the following general formula:

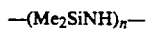

(wherein Me represents a methyl group and n is an integer of not less than 4) in the presence of at least one catalytic compound selected from the group consisting of ammonium salts of arylsulfonic acids and/or aminoarylsulfonic acids and the resulting hexamethyl cyclotrisilazane represented by the formula: —Me$_2$SiNH)$_3$— can be recovered by distilling off the same outside the reaction system. According to the method of the present invention, highly pure hexamethyl cyclotrisilazane can be industrially prepared in good efficiency and in a high yield. In particular, if octamethyl cyclotetrasilazane which can be industrially prepared from cheap dimethyldichlorosilane is used as a starting material, hexamethyl cyclotrisilazane can also be prepared at a low cost. Thus, the method of the present invention has enough practical value in the organic silicon industries.

6 Claims, No Drawings

METHOD FOR PREPARING HEXAMETHYL CYCLOTRISILAZANE

BACKGROUND OF THE INVENTION

The present invention relates to a method for preparing a silazane compound which is industrially important, for instance, as a starting material for preparing a variety of organopolysiloxanes and as a starting material for preparing silicon nitride and silicon carbide nitride.

The silazane compound can be prepared by reacting a halogenosilane with ammonia in an organic solvent. This method for preparing silazane compounds has been known for a long time and is disclosed in J. Am. Chem. Soc., 1948, 70, p. 3888.

According to this method, cyclotrisilazane is obtained as a mixture with other silazane compounds and accordingly the yield of cyclotrisilazane is very low. For instance, when dimethyldichlorosilane is reacted with ammonia, a mixture of hexamethyl cyclotrisilazane and octamethyl cyclotetrasilazane can be prepared.

However, octamethyl cyclotetrasilazane which is included in the resulting mixture has a high melting point in the order of 97° C. and hence is solid at ordinary temperature. For this reason, it solidifies in a condenser through condensation during the usual distillation operation and it is correspondingly difficult to handle and to hence obtain it at a high purity. Under such circumstances, there has been desired to convert it into hexamethyl cyclotrisilazane which may be obtained at a high purity and is a liquid at ordinary temperature from the industrial standpoint.

As an example of a method for selectively preparing cyclotrisilazane, Japanese Patent Publication 63-58838 discloses a method which comprises heating the resulting cyclosilazanes other than cyclotrisilazane in the presence of hydrogen and a catalyst of a Group VIII metal. However, this method suffers from various problems. For instance, hydrogen which is a combustible gas is employed, the catalyst used is very expensive and the yield of the desired compound is low because of the formation of high molecular weight compounds.

In addition, Soviet Plast, (10), 1965 discloses a method for preparing an equilibrium mixture of octamethyl cyclotetrasilazane and hexamethyl cyclotrisilazane by heating octamethyl cyclotetrasilazane over a long time period in the presence of sulfuric acid or ammonium sulfate as a catalyst. However, in this method, the yield of hexamethyl cyclotrisilazane is likewise low because of the formation of polymeric compounds as by-products during establishing the equilibrium and the presence of octamethyl cyclotetrasilazane remaining in the system.

Alternatively, if hexamethyl cyclotrisilazane produced is distilled off outside the system (which is similar to the method of the present invention) in the presence of sulfuric acid or ammonium sulfate, a large amount of polymeric compounds are formed and accordingly the yield of the desired compound is also low as will be demonstrated in the Comparative Examples given below. This means that sulfuric acid or ammonium sulfate is not favorable for the industrial production of hexamethyl cyclotrisilazane.

SUMMARY OF THE INVENTION

The present invention has been developed for solving the foregoing problems associated with the conventional method for preparing hexamethyl cyclotrisilazane and accordingly the object of the present invention is to provide a method for preparing hexamethyl cyclotrisilazane in an industrial scale, at a low cost and in high efficiency.

According to the present invention, the foregoing object can effectively be accomplished by providing a method for preparing hexamethyl cyclotrisilazane which comprises the steps of heating a linear or cyclic silazane compound represented by the following general formula:

$$-(Me_2SiNH)_n-$$

(wherein Me represents a methyl group and n is an integer of not less than 4) in the presence of at least one catalytic compound selected from the group consisting of ammonium salts of arylsulfonic acids and/or aminoarylsulfonic acids and then distilling off the resulting hexamethyl cyclotrisilazane represented by the formula: $-(Me_2SiNH)_3-$, outside the reaction system.

DETAILED EXPLANATION OF THE INVENTION

The silazane compounds used as starting materials in the method of the present invention can be obtained by, for instance, introducing a dimethyldihalogenosilane and an organic solvent into a reactor to form a solution and supplying ammonia to the solution with stirring to thus cause a reaction. The desired silazane compounds can be obtained by treating the resulting reaction solution according to, for instance, a filtration technique to thus give a mixed solution containing, as principal components, hexamethyl cyclotrisilazane and octamethyl cyclotetrasilazane and then subjecting the mixed solution obtained to a separation operation such as distillation.

The silazane compound may be a single silazane compound or a mixture of a plurality of silazane compounds. For instance, the reaction solution per se which comprises a plurality of silazane compounds and is obtained by subjecting a dimethyldihalogenosilane to ammonolysis may be used as a starting material in the method of the present invention without subjecting it to any further separation operation such as distillation.

The silazane compound is introduced into a reactor equipped with a distillation column, a stirring machine and a condenser together with a desired catalyst.

The catalyst used in the method of the present invention comprises at least one catalytic compound selected from the group consisting of ammonium salts of arylsulfonic acids and/or aminoarylsulfonic acids. Examples of the catalytic compounds preferably used in the present invention include those represented by the following general formulae:

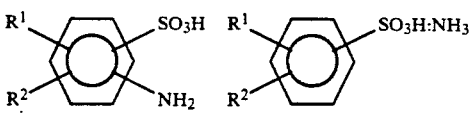

-continued

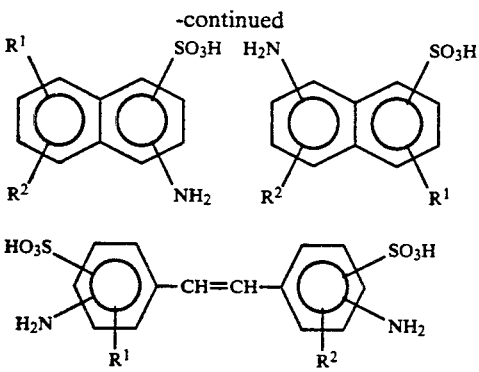

(wherein $R^1$ and $R^2$ each independently represents a hydrogen atom or a lower alkyl group having 1 to 12 carbon atoms) and specific examples of preferred such catalytic compounds are ammonium salts of benzenesulfonic acid, toluenesulfonic acid, dodecylbenzenesulfonic acid or the like,

toluidinesulfonic acid

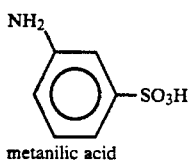

metanilic acid

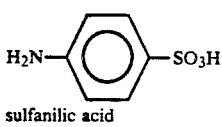

sulfanilic acid

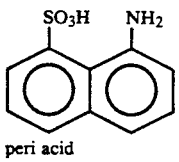

peri acid

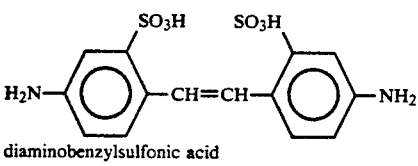

diaminobenzylsulfonic acid

Particularly preferred examples thereof are p-toluidine-m-sulfonic acid, metanilic acid and sulfanilic acid among others. In addition, the foregoing ammonium salts of sulfonic acids may be added to the reaction system by directly adding the corresponding sulfonic acid to the reaction system to react the same with the silazane compound and to thus form the corresponding ammonium salt in the reaction system.

If a catalyst is added, this reaction very rapidly proceeds and, therefore, it is sufficient to add the catalyst in an amount ranging from 0.05 to 10% by weight on the basis of the total weight of the silazane compound used as the starting material. The amount of the catalyst preferably ranges from 0.5 to 5% by weight. This is because if the catalyst is used in an amount of less than 0.05% by weight, the reaction rate is very low, while the use of the catalyst in an amount of more than 10% by weight is not preferred from the economical viewpoint.

After introducing the silazane compound and the catalyst into the reactor, the reaction system is heated under stirring. At the time when the temperature of the reaction system reaches the reflux temperature of the hexamethyl cyclotrisilazane, it is distilled off outside the reaction system. The reaction may be carried out under a reduced pressure, but if the extent of the pressure reduction is extremely low and octamethyl cyclotetrasilazane is used as a starting material, the starting material causes solidification within the condenser as discussed above and, therefore, the pressure in the reaction system desirably ranges from 15 to 500 torr and preferably 20 to 300 torr. The temperature in the reactor preferably controlled to the range of from 80° to 170° C. This is because, if it is less than 80° C., the rate of the formation of hexamethyl cyclotrisilazane is low, while the use of a reaction temperature of more than 170° C. is not preferable from the economical viewpoint.

According to the method of the present invention, silazane compounds other than hexamethyl cyclotrisilazane such as octamethyl cyclotetrasilazane can be converted into hexamethyl cyclotrisilazane through simple processes which comprise heating the silazane compounds in the presence of a catalytic compound and distilling off the resulting hexamethyl cyclotrisilazane outside the reaction system. There are not observed the formation of any polymeric compounds as by-products during the reaction. The resulting hexamethyl cyclotrisilazane is in a liquid state at ordinary temperature, thus it not solidified within the apparatus for preparing the same and correspondingly it can be easily handled.

According to the method of the present invention, highly pure hexamethyl cyclotrisilazane can be industrially prepared in good efficiency and in a high yield.

In particular, if octamethyl cyclotetrasilazane which can be industrially prepared from cheap dimethyldichlorosilane is used as a starting material, hexamethyl cyclotrisilazane can also be prepared at a low cost. Thus, the method of the present invention has enough practical value in the organic silicon industries.

The method of the present invention will be explained in more detail with reference to the following working Examples.

EXAMPLE 1

A 200 ml volume glass flask equipped with a stirring machine, a condenser, a distillation column and a tube for distilling off the resulting product was provided. 73 g of octamethyl cyclotetrasilazane and 3.65 g of p-toluidine-m-sulfonic acid as a catalyst were introduced into the glass flask and the content of the flask was heated to 97° C. The content of the flask was stirred after it was confirmed that the octamethyl cyclotetrasilazane was completely molten. When the internal pressure of the reaction system was reduced to 65 torr with a vacuum pump to obtain a distillate, 68 g of hexamethyl cyclotrisilazane was obtained through the distillation over one hour. The resulting hexamethyl cyclotrisilazane had a high purity in the order of 99.1 GC % and the yield thereof was 93.2%. Thus, highly pure hexamethyl cyclotrisilazane could be obtained at a high yield within a short period of time. Moreover, almost no high boiling point substance remained in the reaction system.

EXAMPLE 2 TO 4

The same procedures as those used in Example 1 were repeated except that the compounds listed in the following Table 1 were substituted for the catalyst used in Example 1 and it was found that a large amount of high boiling point substances were formed and remained in the reaction system. The quantity produced, yield and purity of the resulting hexamethyl cyclotrisilazane are listed in the following Table 1.

TABLE 1

| | Catalyst | Produced (g) | Yield (wt %) | Purity (GC %) |
|---|---|---|---|---|
| Example 2 | H₃C—⟨⟩—SO₃H:NH₃ | 65 | 89.0 | 98.9 |
| Example 3 | H₂N—⟨⟩—SO₃H | 69 | 94.5 | 99.0 |
| Example 4 | SO₃H, NH₂ (naphthalene) | 63 | 86.3 | 99.6 |
| Comparative Example 1 | H₂SO₄ | 45 | 56.2 | 94.5 |
| Comparative Example 2 | (NH₄)₂SO₄ | 41 | 56.2 | 93.2 | following Table 1 were substituted for the catalyst used in Example 1 to give hexamethyl cyclotrisilazane in a high yield. The quantity produced, yield and purity of the resulting hexamethyl cyclotrisilazane are summarized in the following Table 1.

EXAMPLE 5

1000 ml of toluene and 129 g of dimethylsilane were added to a 2 l volume of reactor equipped with a stirring machine and a condenser and ammonia gas having a purity of 99% was supplied to the reactor at a rate of 45 l/hr. with stirring. Since there was observed a rise of the temperature of the reaction system in the course of this operation, the reactor was cooled to maintain the temperature of the system at 50° C. Ammonia gas was supplied to the reaction system for 2 hours. When the reaction solution was filtered and then analyzed by the gas chromatography technique, it was found that the reaction solution comprised 43.24 g of hexamethyl cyclotrisilazane and 21.8 g of octamethyl cyclotetrasilazane.

This reaction solution was transferred to a glass flask provided with a stirring machine, a condenser, a distillation column and a tube for distilling off the resulting product. After the addition of 1.1 g of p-toluidine-m-sulfonic acid, the internal pressure of the reaction system was reduced to 65 torr and the system was heated with stirring to thus give 62.1 g of a distillate through the distillation over one hour. This distillate was analyzed by the gas chromatography technique and it was found that the distillate was hexamethyl cyclotrisilazane having a purity of 99.3 GC % and contained almost no octamethyl cyclotetrasilazane. In addition, almost no highboiling point substance remained in the reaction system.

COMPARATIVE EXAMPLES 1 TO 2

The same procedures as those used in Example 1 were repeated except that sulfuric acid and ammonium

What is claimed is:

1. A method for preparing hexamethyl cyclotrisilazane comprising the steps of heating a linear or cyclic silazane compound represented by the following general formula:

—(Me₂SiNH)$_n$— wherein Me represents a methyl group and n is an integer of not less than 4, in the presence of at least one catalytic compound selected from ammonium salts of arylsulfonic acids and/or aminoarylsulfonic acids and then distilling off the resulting hexamethyl cyclotrisilazane represented by the formula: —(Me₂SiNH)₃—outside the reaction system.

2. The method as set forth in claim 1 wherein the pressure during the reaction is controlled to the range of from 15 to 500 torr.

3. The method as set forth in claim 1 wherein the temperature in the reactor is controlled to the range of from 80° to 170° C.

4. The method as set forth in claim 1 wherein the catalytic compound or the ammonium salt of an arylsulfonic acid and/or the aminoarylsulfonic acid is selected from the group consisting of those represented by the following general formulae:

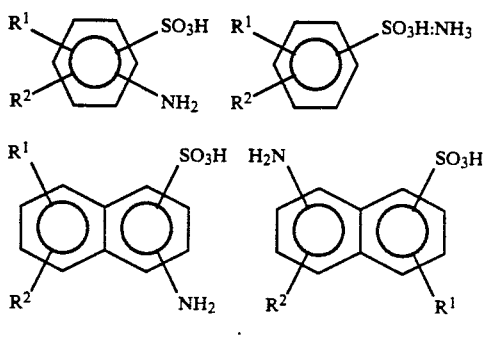

-continued

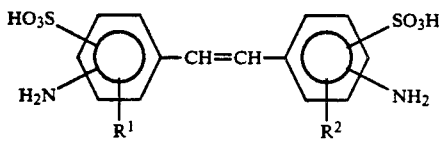

wherein $R^1$ and $R^2$ each independently represents a hydrogen atom or a lower alkyl group having 1 to 12 carbon atoms.

5. The method as set forth in claim 4 wherein the catalytic compound or the ammonium salt of an arylsulfonic acid and/or the aminoarylsulfonic acid is toluidinesulfonic acid, metanilic acid, sulfanilic acid, peri acid or diaminobenzylsulfonic acid.

6. The method as set forth in claim 4 wherein the amount of the catalyst to be added ranges from 0.05 to 10% by weight on the basis of the weight of the silazane compound as the starting material.

* * * * *